United States Patent [19]

Hallenbach et al.

[11] Patent Number: 4,737,515
[45] Date of Patent: Apr. 12, 1988

[54] USE OF TETRAHYDROBENZOTHIENYLUREA DERIVATIVES AS FUNGICIDES

[75] Inventors: Werner Hallenbach, Langenfeld; Hans Lindel, Leverkusen; Wilhelm Brandes, Leichlingen, all of Fed. Rep. of Germany

[73] Assignee: Bayer Aktiengesellschaft, Leverkusen, Fed. Rep. of Germany

[21] Appl. No.: 931,295

[22] Filed: Nov. 14, 1986

[30] Foreign Application Priority Data

Nov. 26, 1985 [DE] Fed. Rep. of Germany ....... 3541630

[51] Int. Cl.$^4$ ............................................. A01N 43/12
[52] U.S. Cl. ................................................... 514/443
[58] Field of Search ......................................... 514/443

[56] References Cited

U.S. PATENT DOCUMENTS

| 3,823,161 | 7/1974 | Lesser | 260/332.2 C |
| 3,989,505 | 11/1976 | Nickell | 71/90 |
| 4,240,820 | 12/1980 | Dickore et al. | 71/67 |
| 4,250,319 | 2/1981 | Karabinos | 71/90 |

FOREIGN PATENT DOCUMENTS

0004931 10/1979 European Pat. Off. .

OTHER PUBLICATIONS

Journal of Pharmaceutical Sciences, vol. 65, No. 5 May 1976, pp. 660–664, Devani et al.
Chemical Abstracts, vol. 92, No. 9, Mar. 3, 1980, p. 650.
Arch. Pharm. (Weinheim) 312, pp. 726–733 (1979).

*Primary Examiner*—Allen J. Robinson
*Attorney, Agent, or Firm*—Sprung, Horn, Kramer & Woods

[57] ABSTRACT

A method of combating fungi which comprises applying to such fungi or to a fungus habitat a fungicidally effective amount of a tetrahydrobenzothienylurea derivative of the formula

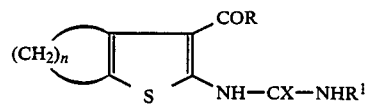

in which
n is 3, 4, 5 or 6,
X is oxygen or sulphur,
R is $C_{1-4}$-alkoxy or hydroxyl, and
$R^1$ is $C_{1-4}$-alkyl.

7 Claims, No Drawings

USE OF TETRAHYDROBENZOTHIENYLUREA DERIVATIVES AS FUNGICIDES

The present invention relates to the use of tetrahydrobenzothienylurea derivatives as fungicides in plant protection.

It has already been disclosed that certain thienylureas, such as, for example, 1-(4,5-dimethyl-3ethoxycarbonyl-2-thienyl)-3-methylurea, possess good fungicidal activity (see, for example U.S. Pat. No. 3,823,161).

Furthermore, 4,5-tetramethyl-thienyl-urea derivatives, such as, for example, 2-phenylureido-3-carbethoxy-4,5-tetramethylene-thiophene, are known agents, for example for promoting the ripening of sugar cane (see German Published Specification No. 2,627,935). Its use as fungicide is not known.

It has been found that, in particular, the compounds of the formula (I)

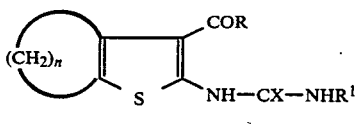

in which
n represents the numbers 3, 4, 5 or 6,
X represents oxygen or sulphur,
R represents $C_1$–$C_4$-alkoxy or hydroxyl and
$R^1$ represents $C_1$–$C_4$-alkyl,
can be used as fungicides in plant protection.

Surprisingly, the tetrahydrobenzothienylurea derivatives of the formula (I) have a substantially more powerful fungicidal action than the compound 1-(4,5-dimethyl-3-ethoxy-carbonyl-2-thienyl)-3-methylurea known from the prior art (see, for example, U.S. Pat. No. 3,823,161).

The $C_1$–$C_4$-alkoxy radical R denotes straight-chain or branched alkoxy having 1 to 4 carbon atoms. Methoxy, ethoxy, n-propoxy, i-propoxy, n-butoxy, i-butoxy, sec.-butoxy and tert.-butoxy may be mentioned as examples.

The $C_1$–$C_4$-alkyl radical $R^1$ denotes straight-chain or branched alkyl having 1 to 4 carbon atoms. Methyl, ethyl, n-propyl, i-propyl, n-butyl, i-butyl, sec.-butyl or tert.-butyl may be mentioned as examples.

X preferably represents oxygen.

Formula (I) gives a general definition of the tetrahydrobenzothienylurea derivatives to be used according to the invention.

In this formula,
n preferably represents the numbers 3, 4, 5 or 6,
X preferably represents oxygen,
R preferably represents hydroxyl, methoxy, ethoxy, n-propoxy, i-propoxy, n-butoxy, i-butoxy, sec.-butoxy or tert.-butoxy and
$R^1$ preferably represents methyl, ethyl, n-propyl, i-propyl, n-butyl, i-butyl, sec.-butyl or tert.-butyl.

Particularly preferred compounds of the formula (I) are those in which
n represents the numbers 3, 4, or 5,
X represents oxygen,
R represents hydroxyl, methoxy, ethoxy, n-propoxy or tert.-butoxy and,
$R^1$ represents methyl, ethyl, i-propyl or n-butyl.

Some of the active compounds to be used according to the invention, of the formula (I), are known and/or can be prepared in a simple manner by known methods (see, for example, EP-OS (European Published Specification) No. 4,931, DE-AS (German Published Specification) No. 2,040,579, DE-AS (German Published Specification No. 2,122,636 (=U.S. Pat. No. 3,823,161), DE-AS (German Published Specification) No. 2,627,935, corresponding to German Application No. P 35 29 247.4 of Aug. 16, 1985). Thus for example, 2-amino-tetrahydrobenzothiophene derivatives can be reacted with isocyanates or isothiocyanates according to the following equation:

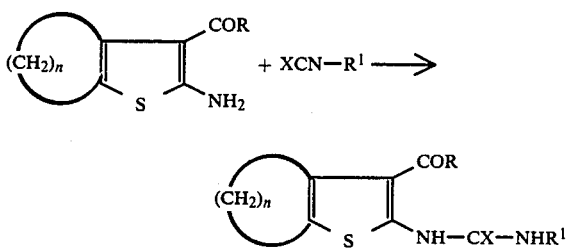

The reaction is usually carried out under atmospheric pressure and at a temperature of 20° C. to 70° C., if appropriate in the presence of an auxiliary base and in the presence of inert diluents, such as, for example, toluene, chloroform and pyridine.

The active compounds to be used according to the invention have a powerful fungicidal action and can be employed in practice for combating undesired fungi. The active compounds are suitable for use as fungicides in plant protection.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation:

Pythium species, such as, for example, *Pythium ultimum;*

Phytophthora species, such as, for example, *Phytophthora infestans;*

Pseudoperonospora species, such as, for example, *Pseudoperonospora humuli* or *Pseudoperonospora cubense;*

Plasmopara species, such as, for example, *Plasmopara viticola;*

Peronospora species, such as, for example, *Peronospora pisi* or *P. brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *P. graminea* (conidia form: Drechslera, syn: Helminthosporium);

Cochliobolus species, such as, for example, *Cochliobolus sativus* (conidia form: Drechslera, syn: Helminthosporium);

Uromyces species, such as, for example, *Uromyces appendiculatus;*

Puccinia species, such as, for example, *Puccinia recondita;*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytris cinerea;*

Septoria species, such as, for example, *Septora nodorum;*

Leptosphaeria species, such as, for example, *Leptosphaeria nodorum;*

Cercospora species, such as, for example, *Cercospora canescens;*

Alternaria species, such as, for example, *Alternaria brassicae* and

Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

The active compounds can be converted to the customary formulations, such as solutions, emulsions, suspensions, powders, foams, pastes, granules, aerosols, very fine capsules in polymeric substances and in coating compositions for seed, and ULV formulations.

These formulations are produced in known manner, for example by mixing the active compounds with extenders, that is, liquid solvents, liquefied gases under pressure and/or solid carriers, optionally with the use of surface-active agents, that is, emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly disperse silicic acid, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. As dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, acaricides and herbicides, and also as mixtures with fertilizers and growth regulators.

The active compounds to be used according to the invention can be used as such, in the form of their formulations or as the use forms prepared therefrom, such as ready-to-use solutions, emulsifiable concentrates, emulsions, foams, suspensions, wettable powders, pastes, soluble powders, dusting agents and granules. They are used in the customary manner, for example by watering, spraying, atomizing, scattering, dusting, foaming, coating and the like. Furthermore, it is possible to apply the active compounds in accordance with the ultra-low volume process or to inject the active compound preparation of the active compound itself into the soil. It is also possible to treat the seeds of plant.

In the treatment of parts of plants, the active compound concentrations in the use forms can be varied within a more substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.001 to 0.02% are required at the place of action.

EXAMPLE A

Botrytis test (bean)/protective

Solvent: 4.7 parts by weight of acetone.

Emulsifier: 0.3 part by weight of alkylaryl polyglycol ether.

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, 2 small pieces of agar covered with *Botrytis cinerea* are placed on each leaf. The inoculated plants are placed in a darkened humid chamber at 20° C. 3 days after the inoculation, the size of the infected spots on the leaves is evaluated.

In this test, clearly superior activity compared to the prior art (A) is shown, for example, by the compound according to Example 7, as follows:

TABLE A

| | Botrytis test (bean)/protective | |
|---|---|---|
| Active compound | | Infestation in % at an active compound concentration of 100 ppm |
| 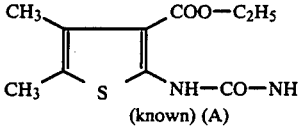 (known) (A) | | 29 |
| 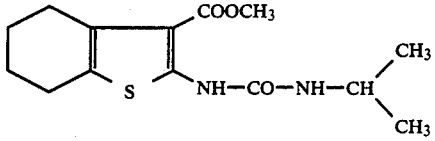 (7) | | 17 |

EXAMPLE B

Botrytis test (grape vine)/protective

Solvent: 4.7 parts by weight of acetone.
Emulsifier: 0.8 part by weight of alkyl-aryl polyglycol ether.

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, 2 small pieces of agar covered with *Botrytis cinerea* are placed on each leaf. The inoculated plants are placed in a darkened humid chamber at 20° C. 3 days after the inoculation, the size of the infected spots on the leaves is evaluated.

In this test, clearly superior activity compared to the prior art (A) is shown, for example, by the compound according to Example 7, as follows:

PREPARATION EXAMPLES

EXAMPLE 1

Preparation of

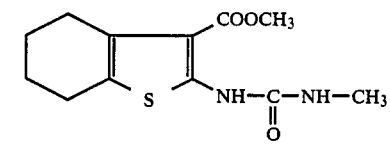

4.5 g (0.021 mol) of 2-amino-3-methoxycarbonyltetrahydrobenzothiophene and 1.4 g (0.024 mol) of methyl isocyanate in 100 ml of dry chloroform are heated under reflux for 24 hours. Thereafter, the chloroform phase is washed with three times 50 ml of water, dried over sodium sulphate and evaporated down. The crude product obtained is recrystallized from ethanol.

Yield: 3.2 g (58% of theory), melting point 167° C. (decomposition).

The following compounds of the formula (I)

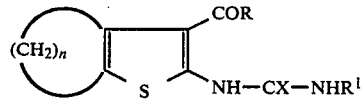

TABLE B

| | Botrytis test (grape vine)/protective | |
|---|---|---|
| Active compound | | Infestation in % at an active compound concentration of 25 ppm |
| (known) (A) 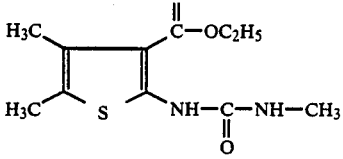 | | 32 |
| 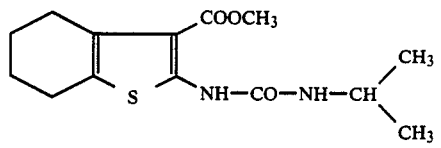 (7) | | 6 | can be prepared analogously to Example 1:

| Example No. | n | R | R' | X | Melting point, °C. |
|---|---|---|---|---|---|
| 2 | 3 | —OC$_2$H$_5$ | CH$_3$ | O | 165 |
| 3 | 3 | —OC$_2$H$_5$ | i-C$_3$H$_7$ | O | 145 |
| 4 | 4 | —OC$_4$H$_9$-t | CH$_3$ | O | 150 |
| 5 | 5 | —OC$_2$H$_5$ | CH$_3$ | O | 148 |
| 6 | 5 | —OC$_2$H$_5$ | i-C$_3$H$_7$ | O | 113 |
| 7 | 4 | —OCH$_3$ | i-C$_3$H$_7$ | O | 165 |
| 8 | 4 | —OCH$_3$ | n-C$_4$H$_9$ | O | 130 |
| 9 | 4 | —OH | i-C$_3$H$_7$ | O | 174 |

It will be understood that the specification and examples are illustrative but not limitative of the present invention and that other embodiments within the spirit and scope of the invention will suggest themselves to those skilled in the art.

We claim:

1. A method of combating fungi selected from the group consisting of Botrytis and Fusarium which comprises applying to such fungi a fungicidally effective amount of a tetrahydrobenzothienylurea derivative of the formula

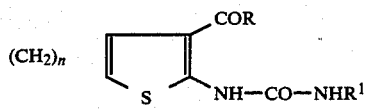

in which
n is 3, 4, 5 or 6,
R is C$_{1-4}$ alkoxy or hydroxyl, and
R$^1$ is C$_{1-4}$ alkyl.

2. The method according to claim 1, in which
R is methoxy, ethoxy, n-propoxy, i-propoxy, n-butoxy, i-butoxy, sec.-butoxy, tert.-butoxy or hydroxyl, and
R$^1$ is methyl, ethyl, n-propyl, i-propyl, n-butyl, i-butyl, sec.-butyl or tert.-butyl.

3. The method according to claim 1, in which
n is 3, 4 or 5,
R is hydroxyl, methoxy, ethoxy, n-propoxy or tert.-butoxy, and
R$^1$ is methyl, ethyl, i-propyl or n-butyl.

4. The method according to claim 1, wherein the derivative is 2-methylureido-3-carbethoxy-4,5-pentamethylene-thiophene of the formula

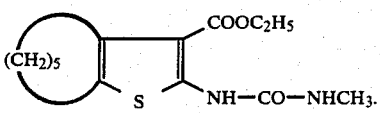

5. The method according to claim 1, wherein the derivative is 2-isopropylureido-3-carbethoxy-4,5-pentamethylene-thiophene of the formula

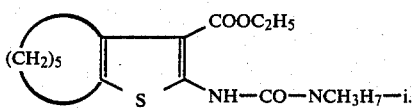

6. The method according to claim 1, wherein the derivative is 2-isopropylureido-3-carbomethoxy-4,5-tetramethylene-thiophene of the formula

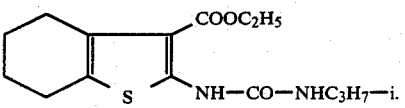

7. The method according to claim 1, wherein the fungus is a Botrytis fungus.

* * * * *